(12) United States Patent
Itai (10) Patent No.: US 12,315,123 B2
(45) Date of Patent: May 27, 2025

(54) IMAGE ANALYSIS DEVICE, ANALYSIS FUNCTION DECISION METHOD, AND ANALYSIS FUNCTION DECISION PROGRAM

(71) Applicant: FUJIFILM Corporation, Tokyo (JP)

(72) Inventor: Yoshinori Itai, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 480 days.

(21) Appl. No.: 17/322,919

(22) Filed: May 18, 2021

(65) Prior Publication Data

US 2021/0272254 A1     Sep. 2, 2021

Related U.S. Application Data

(63) Continuation of application No. PCT/JP2019/045318, filed on Nov. 19, 2019.

(30) Foreign Application Priority Data

Nov. 20, 2018  (JP) .................. 2018-217752

(51) Int. Cl.
*G06T 7/00*     (2017.01)
*G06F 9/4401*   (2018.01)
*G06N 20/00*    (2019.01)
*G16H 30/20*    (2018.01)
*G16H 30/40*    (2018.01)
(Continued)

(52) U.S. Cl.
CPC .............. *G06T 7/00* (2013.01); *G06F 9/4401* (2013.01); *G06N 20/00* (2019.01); *G16H 30/20* (2018.01); *G16H 30/40* (2018.01);
*G06T 2207/20081* (2013.01); *G16H 40/20* (2018.01); *G16H 50/20* (2018.01)

(58) Field of Classification Search
CPC ............ G16H 30/00–40; A61B 6/5294; G06F 19/321
See application file for complete search history.

(56) References Cited

U.S. PATENT DOCUMENTS 9,679,106 B2   6/2017   Yanagida et al.
10,885,391 B2  1/2021   Sakuragi
(Continued)

FOREIGN PATENT DOCUMENTS

JP   2007144151   6/2007
JP   2008210383   9/2008
(Continued)

OTHER PUBLICATIONS

"International Search Report (Form PCT/ISA/210) of PCT/JP2019/045318," mailed on Feb. 18, 2020, with English translation thereof, pp. 1-5.
(Continued)

*Primary Examiner* — Raphael Schwartz
(74) *Attorney, Agent, or Firm* — JCIPRNET (57) ABSTRACT

The image analysis device includes an analysis unit that analyzes input image data using a preset analysis function, and a control unit that, in a case in which a start-up request is received from an exterior, determines an analysis function to be a start-up target among plural analysis functions based on an analysis result obtained by the preset analysis function and a preset condition, and performs control to start-up the determined analysis function.

17 Claims, 5 Drawing Sheets

(51) Int. Cl.
    *G16H 40/20*    (2018.01)
    *G16H 50/20*    (2018.01)

(56) References Cited

U.S. PATENT DOCUMENTS

| | | | |
|---|---|---|---|
| 2007/0063998 A1* | 3/2007 | Mahesh | G16H 30/20 |
| | | | 715/757 |
| 2008/0133596 A1* | 6/2008 | Chang | G16H 40/67 |
| 2008/0199199 A1 | 8/2008 | Kato et al. | |
| 2018/0247709 A1 | 8/2018 | Sakamoto et al. | |
| 2020/0118671 A1 | 4/2020 | Sakamoto et al. | |

FOREIGN PATENT DOCUMENTS

| | | |
|---|---|---|
| JP | 2009268589 | 11/2009 |
| JP | 2011050608 | 3/2011 |
| JP | 2013081713 | 5/2013 |
| JP | 2015159861 | 9/2015 |
| JP | 2017080398 | 5/2017 |
| WO | 2018079246 | 5/2018 |

OTHER PUBLICATIONS

"Written Opinion of the International Searching Authority (Form PCT/ISA/237) of PCT/JP2019/045318," mailed on Feb. 18, 2020, with English translation thereof, pp. 1-11.
Office Action of Japan Counterpart Application, with English translation thereof, issued on Jul. 26, 2022, pp. 1-9.

* cited by examiner

IMAGE ANALYSIS DEVICE, ANALYSIS FUNCTION DECISION METHOD, AND ANALYSIS FUNCTION DECISION PROGRAM

CROSS-REFERENCE TO RELATED APPLICATIONS

This application is a continuation application of International Application No. PCT/JP2019/045318, filed on Nov. 19, 2019, which is incorporated herein by reference in its entirety. Further, this application claims priority from Japanese Patent Application No. 2018-217752, filed on Nov. 20, 2018, the disclosure of which is incorporated by reference herein in their entirety.

BACKGROUND

Technical Field

The present disclosure relates to an image analysis device, an analysis function determination method, and a non-transitory storage medium storing an analysis function determination program.

Related Art

In recent years, in addition to X-ray imaging devices, due to advances in medical devices such as a computed tomography (CT) device, an ultrasound (US) diagnostic device, a magnetic resonance imaging (MRI) device, a positron emission tomography (PET) device, and a single-photon emission computed tomography (SPECT), it has been possible to diagnosis image using three-dimensional medical images having high resolution that has high quality. In particular, since a region of the lesion can be accurately specified by the image diagnosis using the three-dimensional medical image, appropriate treatment has come to be performed based on the specified result. In addition, by analyzing the three-dimensional medical image with various analysis applications, the region, position, volume, and the like of lesions included in the medical image can be extracted and acquired as the analysis result. As described above, the analysis result generated by the analysis processing is associated with the examination information such as the patient name, gender, age, the modality by which the medical image is acquired, and the like stored in the database, and used for diagnosis.

On the other hand, recent image diagnostic system can be roughly divided into image interpretation terminals for interpreting the medical images and image analysis devices for performing detailed analysis with respect to medical images. In many cases, a user such as an image interpreter and a doctor confirms the presence or absence of a disease with the image interpretation terminal, and performs detailed analysis with respect to the found disease with the image analysis device to collect information for more accurate diagnosis. In a case in which the image analysis device comprises the same image interpretation function as the image interpretation terminal, the image analysis device can be operated independently. As such an image analysis device, for example, image analysis devices disclosed in JP2009-268589A, JP2015-159861A, and JP2007-144151A have been proposed.

In a case in which the image analysis device is to be started up from another device such as the image interpretation terminal, the image analysis device is started up from the user interface mounted on the other device as a starting-up point. Therefore, the image analysis device can be started up without interrupting the workflow, so that the image interpreter can perform image interpretation efficiently.

On the other hand, the number of analysis functions performed by one examination has a tendency to increase. For example, in a case in which the head CT is imaged, analysis such as cerebrovascular extraction, dental analysis, and perfusion can be performed. In addition, in a case in which the cardiac CT is imaged, coronary artery analysis, cardiac function analysis, calcification score, ablation analysis and the like can be performed. In recent years, since a wide range of analysis methods have been created and preoperative simulation functions have become widespread, there is high possibility that the number of the analysis functions of image analysis devices will increase in the future. In such a situation, in a case in which the image analysis device is started up, a number of analysis functions are started up, so that the load in a case of starting-up may increase and the starting-up time may be long.

JP2009-268589A, JP2015-159861A, and JP2007-144151A disclose that the analysis function related to the examination is decided based on the examination information or the image accessory information, and the decided analysis function is started up. For example, in a case in which the cardiac CT is imaged, only the analysis function related to cardiac examination such as coronary artery analysis, cardiac function analysis, calcification score, ablation analysis and the like is started up.

However, the image interpreter does not use all the analysis functions related to the examination, and the necessary analysis functions are limited depending on the medical condition of the patient. Therefore, by starting up the analysis functions that are not used, an unnecessary load in a case of starting-up and starting-up time have occurred.

SUMMARY

The present disclosure has been made in view of the above circumstances, and is to provide an image analysis device, an analysis function determination method, and a non-transitory storage medium storing an analysis function determination program, which are capable of reducing a load in a case of starting-up and shortening a starting-up time.

An image analysis device according to an aspect of the present disclosure comprises an analysis unit that analyzes input image data using a preset analysis function, and a control unit that, in a case in which a start-up request is received from an exterior, determines an analysis function to be a start-up target among a plurality of analysis functions based on an analysis result obtained by the preset analysis function and a preset condition, and performs control to start-up the determined analysis function.

In the image analysis device according to the aspect of the present disclosure, the control unit may set the preset analysis function based on at least one of the image data or header information of the image data.

Further, the control unit may start up the analysis function determined as the start-up target in a background, and fully starts up the analysis function that has already been started up in the background in a case in which a full start-up request is further received from the exterior.

Further, the control unit may cause the analysis function that has been started up in the background to perform analysis processing of the image data in the background.

Further, the full start-up request from the outside may include identification information of the analysis function, and the control unit may determine the analysis function to be fully started up based on the identification information.

Further, the image analysis device according to the aspect of the present disclosure may further comprise a storage unit that stores the analysis result obtained by the preset analysis function, in which the control unit outputs the analysis result stored in the storage unit in a case in which the analysis result obtained by the started-up analysis function is stored in the storage unit.

Further, the preset condition may be updated by learning.

An analysis function decision method according to another aspect of the present disclosure comprises analyzing input image data using a preset analysis function, and in a case in which a start-up request is received from an exterior, determining an analysis function to be a start-up target among a plurality of analysis functions based on an analysis result obtained by the preset analysis function and a preset condition, and starting up the determined analysis function.

A non-transitory storage medium according to still another aspect of the present disclosure stores a program executable by a computer to perform analysis function determination processing, the analysis function determination processing comprises: analyzing input image data using a preset analysis function, and in a case in which a start-up request is received from an exterior, determining an analysis function to be a start-up target among a plurality of analysis functions based on an analysis result obtained by the preset analysis function and a preset condition, and starting up the determined analysis function.

According to the present disclosure, it is possible to provide an image analysis device, an analysis function decision method, and a non-transitory storage medium storing an analysis function decision program, which are capable of reducing a load in a case of starting-up and shortening a starting-up time.

DETAILED DESCRIPTION

Figure 1:
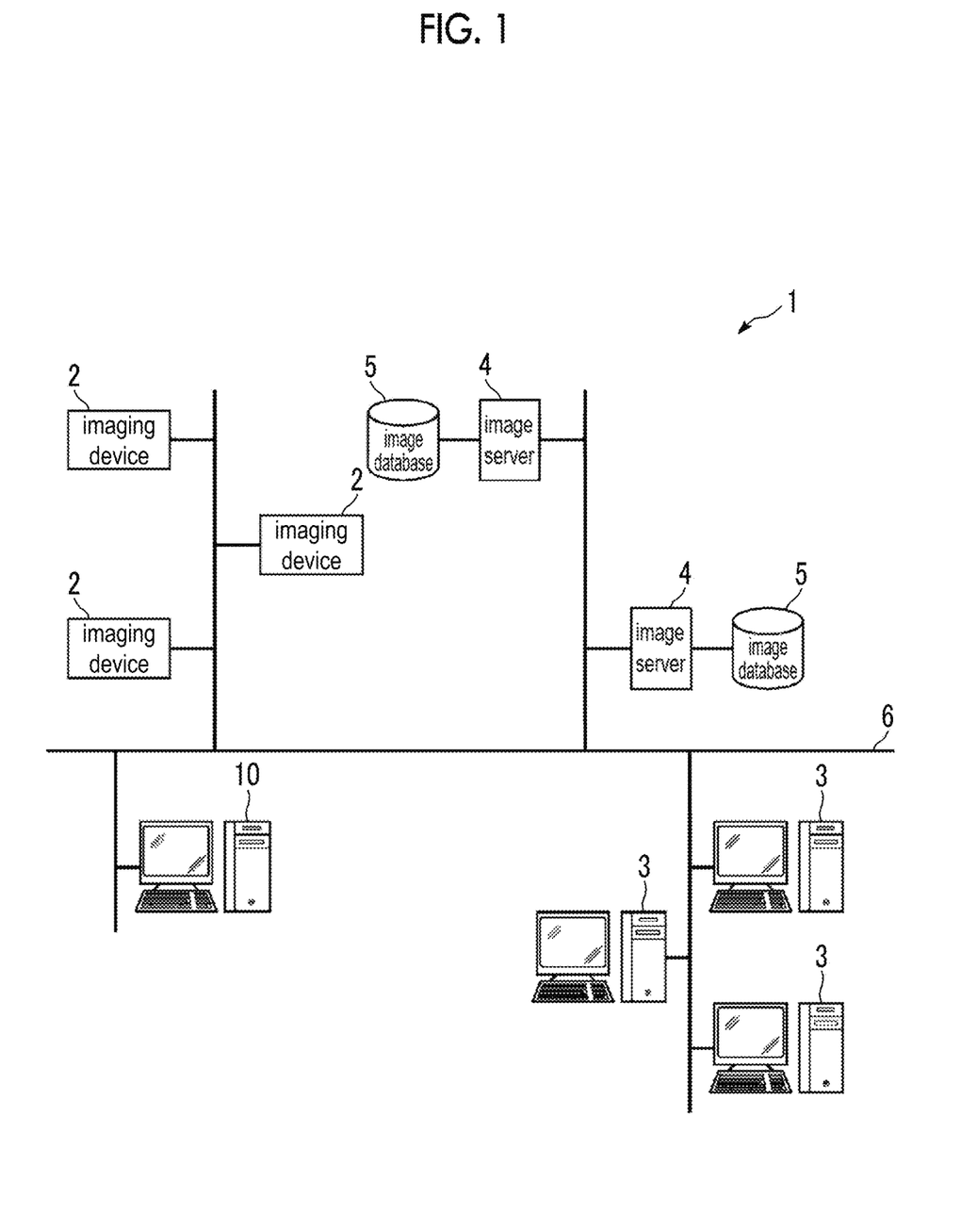
FIG. 1 is a diagram showing a schematic configuration of an image diagnostic system to which an image analysis device according to an embodiment of the present disclosure is applied.

Hereinafter, the embodiment of the present disclosure will be described with reference to the figures. FIG. 1 is a diagram showing a schematic configuration of an image diagnostic system to which an image analysis device according to an embodiment of the present disclosure is applied. An image diagnostic system 1 shown in FIG. 1 is a system that performs imaging of an examination target part of a subject, a storage of medical image acquired by imaging, interpreting of the medical image by an image interpreter, and the like based on based on an examination order from a doctor in a clinical department using a known ordering system.

As shown in FIG. 1, the image diagnostic system 1 is configured in which a plurality of modalities (imaging devices) 2, a plurality of image interpretation workstations (WS) 3 which are image interpretation terminals, an image server 4, an image database 5, and an image analysis workstation (WS) 10 which is the image analysis device according to the present embodiment are connected to be able to communicate with each other via a network 6.

Each device is a computer in which an application program that functions as a component of the image diagnostic system 1 is installed. The application program is recorded in a recording medium such as a digital versatile disc (DVD) or a compact disc read only memory (CD-ROM) to be distributed, and is installed in the computer from the recording medium. Alternatively, the application program is stored in a storage device of a server computer connected to the network or in a network storage in a state of being accessible from the outside, and is downloaded and installed in the computer as necessary.

The modality 2 is a device that generates a medical image that represents a diagnosis target part by imaging a part to be diagnosed of the subject. Specifically, the modality 2 is a CT device, an MRI device, a PET device, and the like. The medical image generated by the modality 2 is transmitted and stored in the image server 4.

The image interpretation WS 3 is a computer used by the image interpreter of the medical image to interpret a medical image, and is configured by a processing device, a high-definition display, and an input device such as a keyboard and a mouse. In the image interpretation WS 3, each processing of a browsing request of the medical image with respect to the image server 4, various image processing with respect to the medical image received from the image server 4, display of the medical image, transfer processing of the medical image with respect to the image analysis WS 10, an image analysis request with respect to the image analysis WS 10, display of an image analysis result is performed by executing a software program for each processing.

The image server 4 is a device in which a software program that provides a database management system (DBMS) function is installed in a general-purpose computer that has a relatively high processing capacity. Further, the image server 4 comprises a large-capacity storage in which the image database 5 is configured. This storage may be a large-capacity hard disk device connected to the image server 4 via a data bus, or may be a disk device connected to a network attached storage (NAS) and a storage area network (SAN) connected to network 6. In a case in which the image server 4 receives a registration request of the medical image from the modality 2, the image server 4 arranges the medical image in a format for database and registers the arranged medical image in the image database 5.

The image data and accessory information of the medical image acquired by the modality 2 are registered in the image database 5 based on the digital imaging and communications in medicine (DICOM) format. Examples of the accessory information may include information such as an image ID for identifying individual medical images, a patient identification (ID) for identifying the subject, an examination ID for identifying the examination, a unique ID (UID: unique identification) which is assigned to each medical image, examination date and examination time when the medical image is generated, the type of modality used in the examination to acquire the medical image, patient information such as patient name, age, gender, or the like, examination part (imaged part), imaging information (imaging protocol, imaging sequence, imaging method, imaging conditions, use of contrast medium, or the like), and series number or collection number in a case in which a plurality of medical images are acquired in one examination.

In a case in which the browsing request is received from the image interpretation WS 3 via the network 6, the image server 4 searches for the medical image registered in the image database 5 and transmits the extracted medical image to the image interpretation WS 3 that is a request source.

The network 6 is a wired or wireless local area network that connects various devices in the hospital. In a case in which the workstation 3 for the image interpreter is installed in another hospital or clinic, the network 6 may be configured such that the local area networks of hospitals are connected to each other by the Internet or a dedicated line. In any case, it is preferable that the network 6 have a configuration capable of realizing high-speed transfer of medical images such as an optical network.

Hereinafter, the image analysis WS 10, which is the image analysis device according to the present embodiment, will be described in detail. The image analysis WS 10 is a workstation in which an analysis function decision program according to the present embodiment is installed in one computer. The computer may be a workstation or a personal computer directly operated by the doctor or the image interpreter who performs a diagnosis, or a server computer connected to the workstation or the personal computer via the network. The analysis function decision program is recorded on a recording medium such as a DVD, a CD-ROM, or the like and is distributed, and is installed in the computer from the recording medium. Alternatively, the application program is stored in a storage device of a server computer connected to the network or in a network storage in a state of being accessible from the outside, and is downloaded and installed in the computer as necessary.

Figure 2:
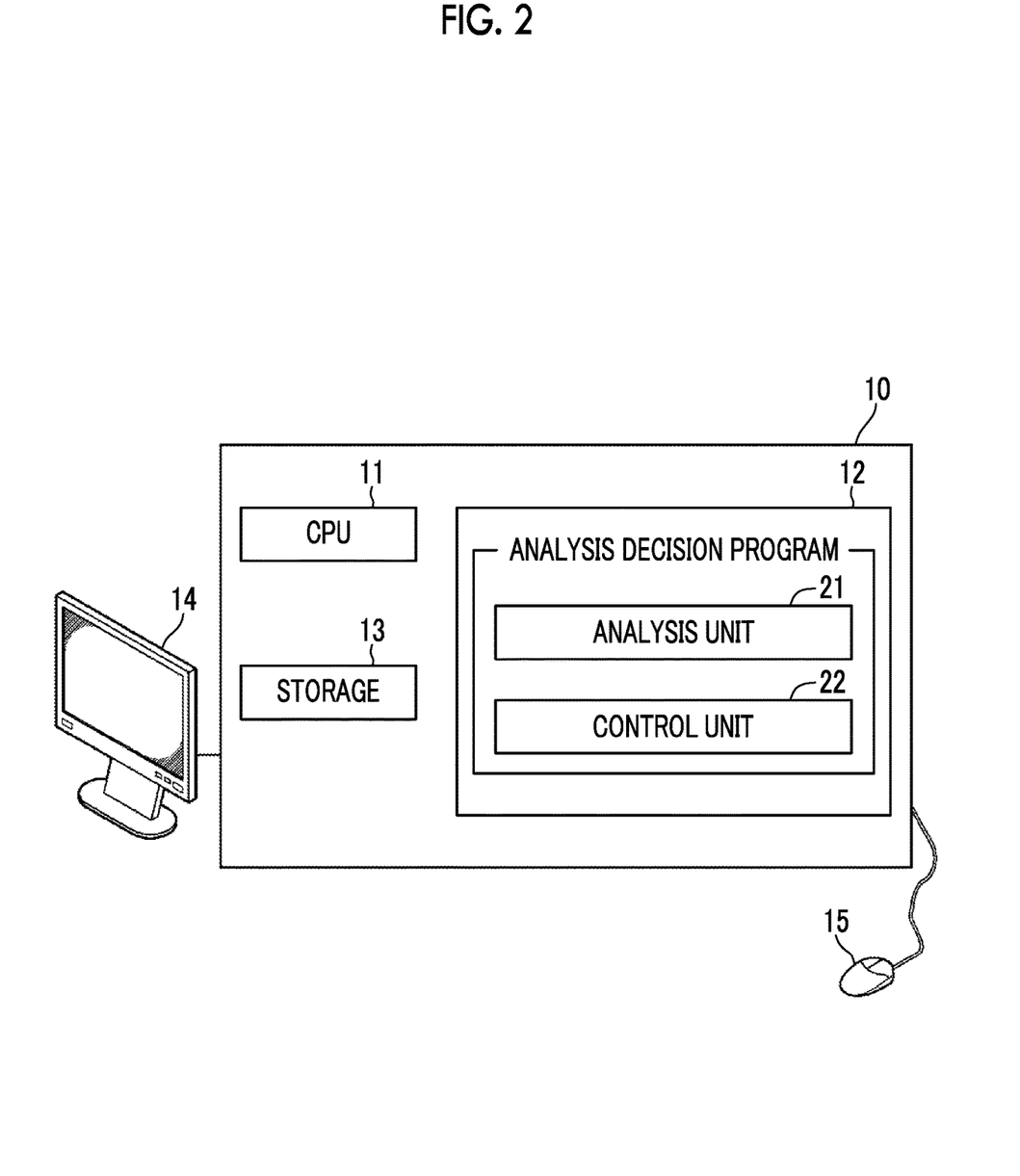
FIG. 2 is a diagram showing a schematic configuration of the image analysis device according to the embodiment of the present disclosure.

FIG. 2 is a diagram showing a schematic configuration of the image analysis WS (image analysis device) 10 according to the first embodiment according to the technique of the present disclosure, which is realized by installing the analysis function decision program in the computer. As shown in FIG. 2, the image analysis WS 10 comprises a central processing unit (CPU) 11, a memory 12, and the storage 13 as the configuration of a standard workstation. Also, the image analysis WS 10 is connected with a display 14 such as a high-definition liquid crystal display, and an input unit 15 such as a keyboard or a mouse.

The storage 13 includes the storage device such as a hard disk, and a solid state drive (SSD). The storage 13 stores various information including the medical image and the information necessary for processing which are acquired via the network 6.

The analysis function decision program is stored in the memory 12. The analysis function decision program defines, as processing executed by the CPU 11, an analysis processing of analyzing input image data by a preset analysis function, and a control processing of, in a case in which a start-up request is received from an outside, deciding an analysis function to be a start-up target among a plurality of the analysis functions based on an analysis result obtained by the preset analysis function and a preset condition, and controlling to start the decided analysis function. The CPU 11 executes processing in accordance with the program, and the computer functions as an analysis unit 21 and a control unit 22.

In the present embodiment, the CPU 11 executes the function of each unit by the analysis function decision program, but as a general-purpose processor that executes software and functions as various processing units, in addition to the CPU 11, a programmable logic device (PLD), which is a processor of which a circuit configuration can be changed after manufacturing, such as a field programmable gate array (FPGA) or the like, can be used. Further, the processing of each unit may be executed by a dedicated electric circuit or the like, which is a processor having a circuit configuration specially designed to execute a specific processing, such as an application specific integrated circuit (ASIC).

One processing unit may be configured by one of these various processors or may be configured by a combination of two or more processors of the same type or different types (for example, a plurality of FPGAs or a combination of the CPU and the FPGA). Alternatively, a plurality of processing units may be configured by one processor. As an example in which a plurality of processing units are configured by one processor, first, as represented by a computer such as a client or a server, there is a form in which one processor is configured by a combination of one or more CPUs and software and this processor functions as a plurality of processing units. Second, as represented by a system on chip (SoC), there is a form in which a processor is used in which the functions of the entire system including a plurality of processing units are realized by a single integrated circuit (IC) chip. As described above, various processing units may be configured by one or more various processors above as a hardware structure.

Furthermore, the hardware structures of these various processors are, more specifically, an electric circuit (circuitry) in which circuit elements such as semiconductor elements are combined.

Figure 3:
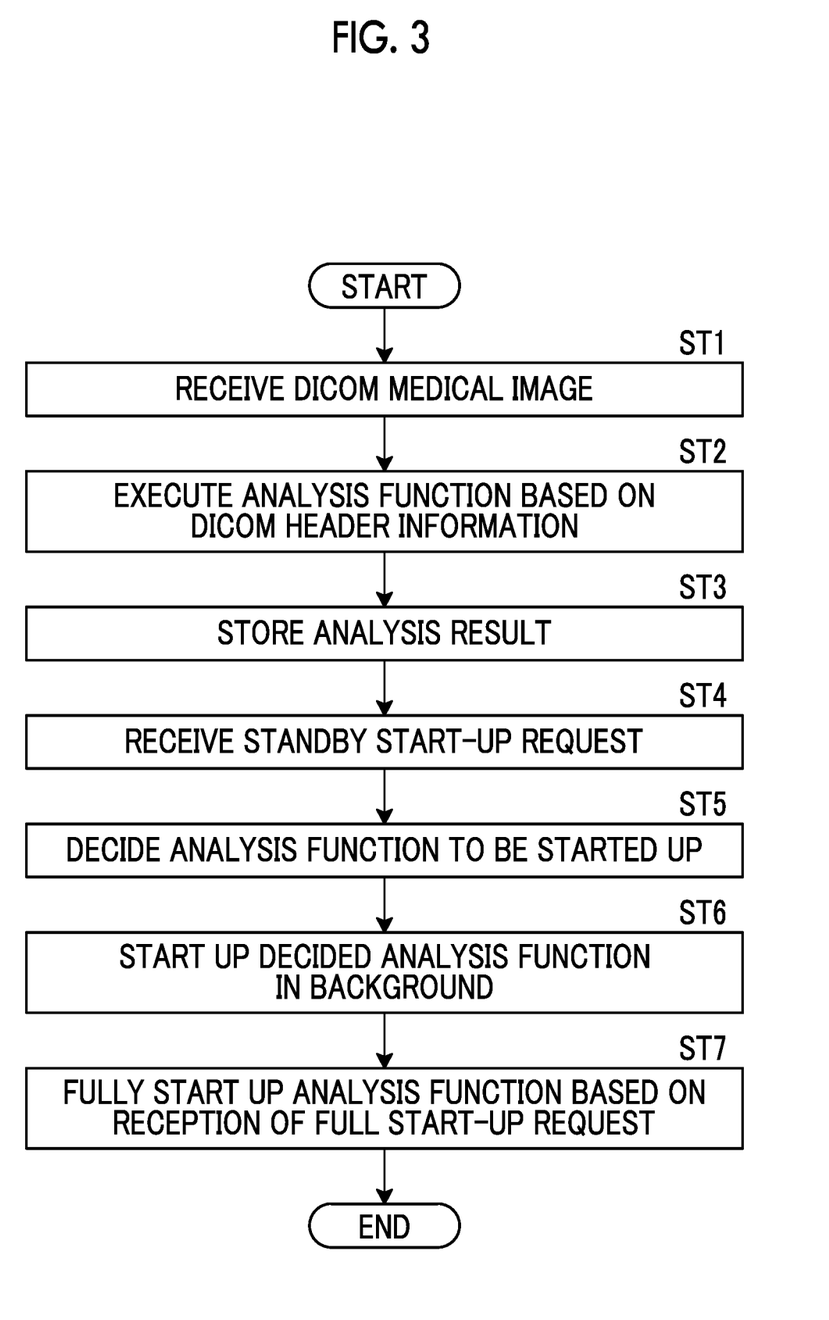
FIG. 3 is a flowchart showing a process performed in a first embodiment.

Next, the processing performed in the present embodiment will be described. FIG. 3 is a flowchart showing the processing performed in the first embodiment.

In a case in which the image interpreter of the medical image tries to browse the medical image in the image interpretation WS 3, the image interpretation WS 3 transmits the browsing request of the medical image with respect to the image server 4, and the image server 4 receives the medical image data in the DICOM format. In this case, the image interpretation WS 3 transfers the received medical image data to the image analysis WS 10. The image analysis WS 10 receives the medical image data from the image interpretation WS 3 (step ST1).

The analysis unit 21 of the image analysis WS 10 performs analysis by the preset analysis function based on the image header information of the medical image data in the DICOM format (step ST2), and stores the analysis result in the storage 13 (step ST3).

For example, in a case in which the medical image is a cardiac CT image, it is possible to automatically determine that the received medical image is the cardiac CT image based on information such as the type of modality 2 that performs imaging, the series description, the number of slices, and the like. In the case of the cardiac CT image, cardiac system analysis functions such as coronary artery analysis, cardiac function analysis, and calcification score are automatically executed, and the image data of the image that shows each analysis result is stored in the storage 13. In addition, data of an analysis value calculated by each analysis function (stenosis rate and plaque amount in a case of the coronary artery analysis, ejection fraction (EF) and single cardiac output in a case of the cardiac function analysis, and a score value in a case of the calcification score) is stored in the storage 13.

Figure 4:
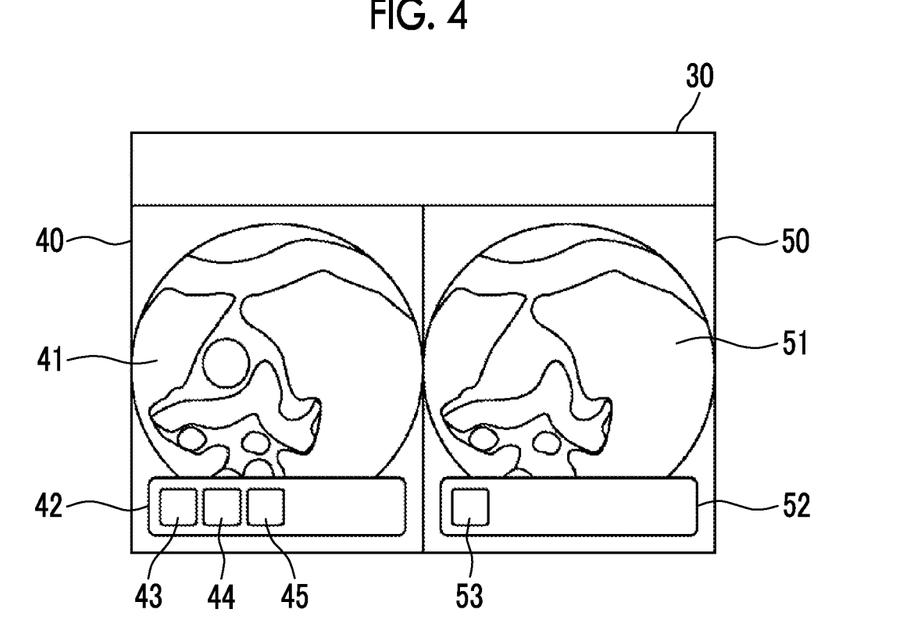
FIG. 4 is a diagram showing a display example of an image in an image interpretation workstation.

In a case in which the medical image is displayed on the image interpretation WS 3, various user interfaces (UI) are displayed together with the medical image on the display of the image interpretation WS 3. In FIG. 4, a display example of the image in this case is shown as an example. As shown in FIG. 4, an entire screen 30 is roughly divided into two types of image display regions of a left image display region 40 and a right image display region 50.

The left image display region 40 comprises an image display region 41 and an analysis function button display frame 42. An analysis function button for executing the analysis function that is executable with respect to the medical image displayed in the image display region 41 is displayed within the analysis function button display frame 42. Here, as an example, an example is shown in which the cardiac CT image is displayed in the image display region 41, and three analysis function buttons (coronary artery analysis button 43, cardiac function analysis button 44, and calcification score button 45) for executing three types of analysis functions (coronary artery analysis, cardiac function analysis, and calcification score) that are executable with respect to the cardiac CT image are displayed within the analysis function button display frame 42.

Similarly, the right image display region 50 comprises an image display region 51 and an analysis function button display frame 52. An analysis function button for executing the analysis function that is executable with respect to the medical image displayed in the image display region 51 is displayed in the analysis function button display frame 52. Here, as an example, an example is shown in which one analysis function button 53 is displayed in the analysis function button display frame 52.

Further, after the image is displayed, the image interpretation WS 3 transmits a standby start-up request of the analysis function to the image analysis WS 10. In a case in which the standby start-up request is received from the image interpretation WS 3 (step ST4), the control unit 22 of the image analysis WS 10 decides the analysis function to be the start-up target among the plurality of analysis functions based on the analysis result in step ST2 and the preset condition (step ST5) and starts the decided analysis function in a background (step ST6).

Here, the start of the background means a state in which the software that controls the analysis function in the image analysis WS (image analysis device) 10 is started up and the screen display of the analysis function corresponding to the image interpretation WS 3 is not performed. Further, in step ST5, the preset condition for deciding the analysis function to be the start-up target means a condition set based on learning data based on the information on the analysis function really necessary for the user (image interpreter) with respect to the medical image in a case of past start of the image analysis WS 10. For example, in a case in which a cardiac CT examination is performed, it is assumed that coronary artery analysis, cardiac function analysis, and calcification score are executed, but an abdominal examination may also be necessary and fat analysis may be executed. In such a case, by accumulating the combination data of the image header information and the actual necessary analysis function, and performing learning using this combination data, it is possible to decide the analysis function necessary for the image header information with high accuracy.

In step ST6, for example, in a case in which the medical image is the cardiac CT image, the stenosis rate is low, and the EF is low, it is assumed that the details of these analysis states are observed, so that the coronary artery analysis and the cardiac function analysis are started up in the background.

Figure 5:
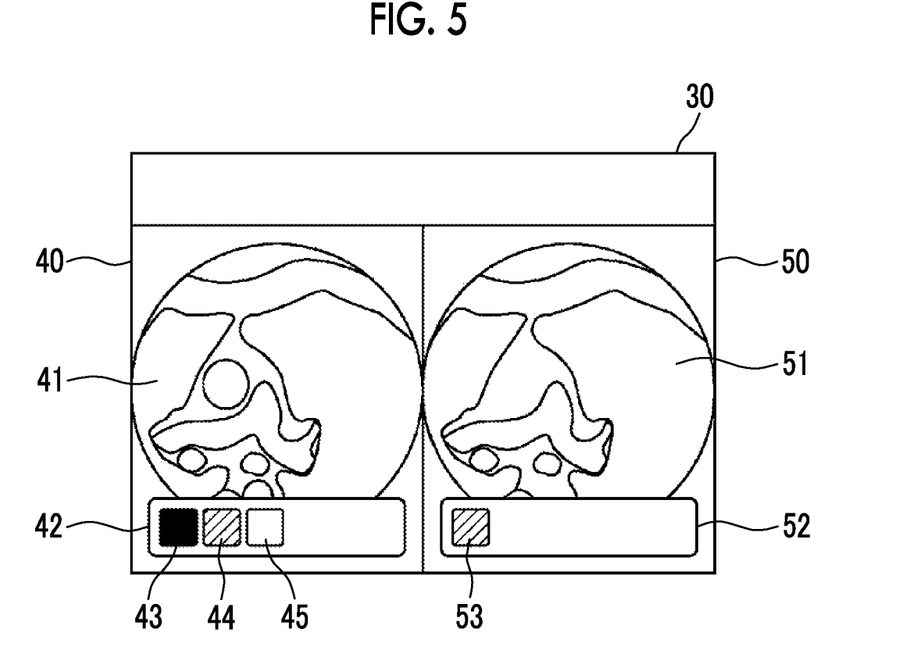
FIG. 5 is a diagram showing another display example of the image in the image interpretation workstation.

In this case, as shown in FIG. 5, the display color of the analysis function button corresponding to the standby started-up analysis function is displayed on the display of the image interpretation WS 3 in different colors in accordance with the standby start-up state. Here, the analysis function button before the standby start-up is displayed in white, the analysis function button during standby starting-up up is displayed in gray (hatched display in the FIG. 5), and the analysis function button that has already been standby started up is displayed in black.

For example, in a case in which the cardiac CT image is displayed in the image display region 41 of the left image display region 40, and three analysis function buttons (coronary artery analysis button 43, cardiac function analysis button 44, and calcification score button 45) for executing three types of analysis functions (coronary artery analysis, cardiac function analysis, and calcification score) that are executable with respect to the cardiac CT image are displayed within the analysis function button display frame 42, in a case in which the coronary artery analysis and the cardiac function analysis are decided as the start-up target, in accordance with the standby start-up state, the coronary artery analysis button 43 corresponding to the coronary artery analysis that has already been standby started up is displayed in black, and the cardiac function analysis button 44 corresponding to the cardiac function analysis during standby starting-up up is displayed in gray. Similarly, the analysis function button in the right image display region 50 is also displayed in a display color in accordance with the standby start-up state.

Here, the control unit 22 may perform analysis processing of the image data in the background by the analysis function that has already been started up in the background.

In a case in which the analysis function button that has already been standby started up (for example, the coronary artery analysis button 43 in FIG. 5) is selected and input in the image interpretation WS 3, the full start-up request of the selected analysis function is transmitted from the image interpretation WS 3 to the image analysis WS 10. In this case, the identification information of the analysis function to be started up is attached to the data indicating the full start-up request.

In a case in which the full start-up request is received from the image interpretation WS 3, the control unit 22 of the image analysis WS 10 performs the full start-up of the analysis function requested that has been the fully started up based on the identification information in the data indicating the full start-up request (step ST7). Here, the full start-up means a state in which the software that controls the analysis function in the image analysis WS (image analysis device) 10 is started up and the screen display of the analysis function corresponding to the image interpretation WS 3 is possible. Then, the analysis result of the fully started-up analysis function is transmitted to the image interpretation WS 3.

Figure 6:
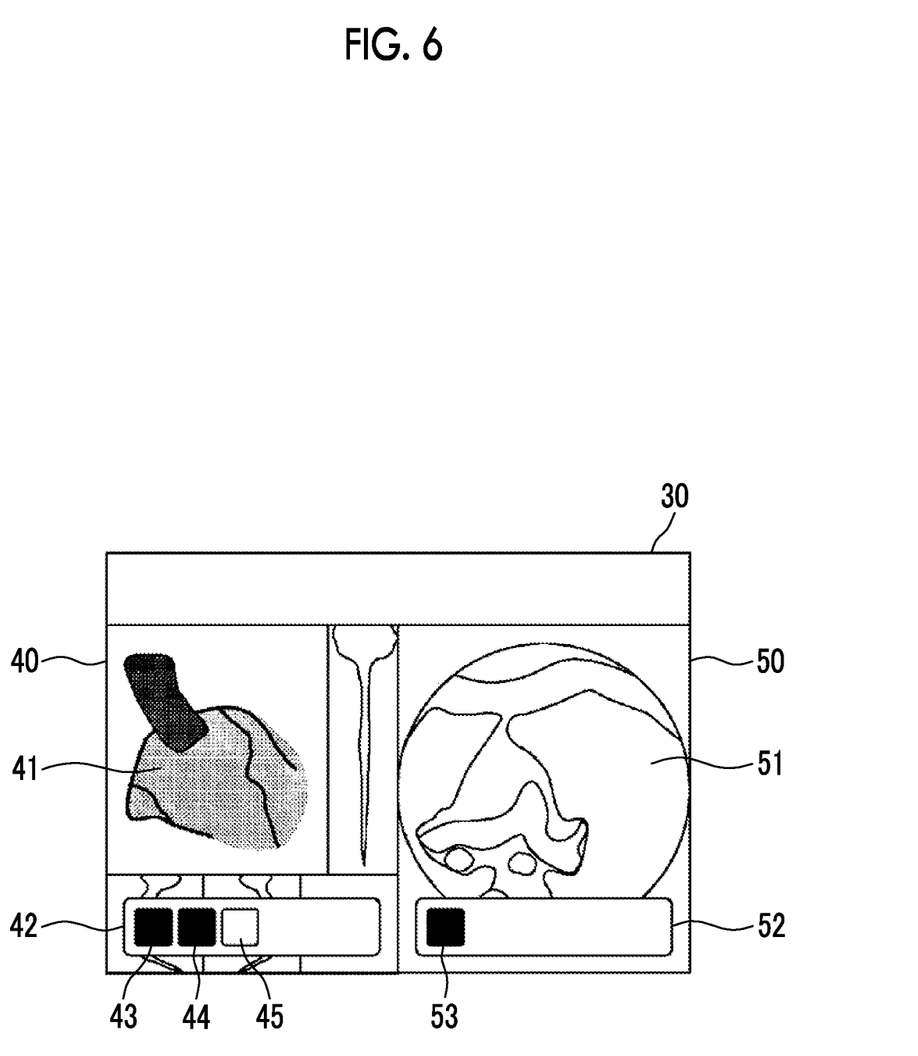
FIG. 6 is a diagram showing still another display example of the image in the image interpretation workstation.

For example, in a case in which the coronary artery analysis button 43 is selected and input in the screen state shown in FIG. 5, the control unit 22 fully starts up the coronary artery analysis among the analysis functions that have already been standby started up, and transmits the result of the coronary artery analysis to the image interpretation WS 3. In a case in which the result of the coronary artery analysis is received, the image interpretation WS 3 displays the result of the coronary artery analysis in the image display region 41 of the left image display region 40, as shown in FIG. 6.

In this case, in a case in which the analysis result of the fully started-up analysis function has already been acquired in step ST2 and the data of the analysis result is stored in the storage 13, the control unit 22 may not newly perform the analysis processing and may transmit the stored analysis result to the image interpretation WS 3.

In the image diagnostic system according to the present embodiment, the input image data is analyzed by the preset analysis function, in a case in which the start-up request is received from the outside, only the necessary analysis function among the plurality of the analysis functions is started up based on the analysis result obtained by the preset analysis function and the preset condition, so that it is possible to reduce the load in a case of starting-up and shorten the starting-up time of the image analysis WS 10.

Although the technique of the present disclosure has been described above based on the preferred embodiment, the image analysis device according to the present disclosure is not limited to the above embodiment, and various changes and modifications which are made from the configuration of the above embodiment are also included in the technical scope of the present disclosure. Further, the technique of the present disclosure extends to a storage medium that non-temporarily stores the program, in addition to the program.

The disclosure of JP2018-217752A filed on Nov. 20, 2018 is incorporated herein by reference in its entirety. All documents, patent applications, and technical standards mentioned herein are incorporated herein by reference to the same extent as a case in which each individual document, patent application, and technical standard are specifically and individually noted to be incorporated by reference.

What is claimed is:

1. An image analysis device comprising at least one processor, wherein the processor is configured to:
analyze input image data using a preset analysis function;
in a case in which a standby start-up request is received from an exterior terminal device, determine an analysis function to be a start-up target among a plurality of analysis functions based on an analysis result obtained by the preset analysis function and a preset condition, and perform control to start-up the determined analysis function in a background such that an analysis result of the determined analysis function is not able to be displayed and an icon corresponding to the determined analysis function is displayed in a first format on a screen of the exterior terminal device; and
in a case in which a full start-up request is further received from the exterior terminal device in response to the icon corresponding to the determined analysis function being selected, fully start up the determined start-up analysis function that has already been started up in the background such that the fully started-up analysis function and the analysis result thereof are able to be displayed and the icon corresponding to the determined analysis function is displayed in a second format different from the first format on the screen of the exterior terminal device.

2. The image analysis device according to claim 1, wherein the processor is configured to select the preset analysis function based on at least one of the image data or header information of the image data.

3. The image analysis device according to claim 1, wherein the processor is configured to cause the background started-up analysis function that has been started up in the background to perform analysis processing of the image data in the background.

4. The image analysis device according to claim 1, wherein the full start-up request from the exterior terminal device includes identification information of the background started-up analysis function, and
the processor is configured to determine the background started-up analysis function to be fully started up based on the identification information.

5. The image analysis device according to claim 1, further comprising a storage configured to store the analysis result obtained by the preset analysis function,
wherein the processor is configured to output a started-up analysis result stored in the storage in a case in which the started-up analysis result obtained by the started-up analysis function is stored in the storage.

6. The image analysis device according to claim 1, wherein the preset condition is updated by learning.

7. The image analysis device according to claim 1, wherein the processor is configured to:
in a case in which another standby start-up request is received from another exterior terminal device, determine two or more analysis functions to be start-up targets among the plurality of the analysis functions based on the analysis result obtained by the preset analysis function and the preset condition, and perform control to start-up at least one of the determined analysis functions in the background.

8. The image analysis device according to claim 7, wherein the processor is configured to:
fully start up at least one of the background started-up analysis functions in a case in which a full start-up request is further received from the another exterior terminal device.

9. The image analysis device according to claim 8, wherein the full start-up request from the exterior terminal device includes identification information of the at least one of the background started-up analysis functions, and
the processor is configured to determine the at least one of the background started-up analysis functions to be fully started up based on the identification information.

10. The image analysis device according to claim 1, wherein the input image data is a medical image in a medicine format, and
wherein the processor analyzes the input image data by the preset analysis function based on image header information of the input image data in the medicine format.

11. The image analysis device according to claim 1, wherein the preset condition is a condition set based on learning data accumulated by a plurality of fully started-up analysis functions performed in the past and image header information corresponding thereto.

12. The image analysis device according to claim 11, wherein the processor is further configured to:
update the learning data according to image header information of the input image data and the fully started-up analysis function.

13. The image analysis device according to claim 1, wherein the image analysis device concurrently displays a first icon corresponding to a first analysis function and a second icon corresponding to a second analysis function on the screen, wherein the second icon is different from the first icon, and wherein the second analysis function is different from the first analysis function, wherein the first icon is displayed in the first format corresponding to the standby start-up request, and wherein the second icon is displayed in the second format corresponding to the full start-up request.

14. The image analysis device according to claim 13, wherein the first icon is displayed in the second format switched from the first format on the screen after the first analysis function is fully started up.

15. The image analysis device according to claim 1, wherein the icon corresponding to the determined analysis function is displayed in a third format different from the first format and the second format before the standby start-up request is received.

16. An analysis function determination method comprising:

analyzing input image data using a preset analysis function;

in a case in which a standby start-up request is received from an exterior terminal device, determining an analysis function to be a start-up target among a plurality of analysis functions based on an analysis result obtained by the preset analysis function and a preset condition, and starting up the determined analysis function in a background such that an analysis result of the determined analysis function is not able to be displayed and an icon corresponding to the determined analysis function is displayed in a first format on a screen of the exterior terminal device; and in a case in which a full start-up request is further received from the exterior terminal device in response to the icon corresponding to the determined analysis function being selected, fully starting up the determined start-up analysis function that has already been started up in the background such that the fully started-up analysis function and the analysis result thereof are able to be displayed and the icon corresponding to the determined analysis function is displayed in a second format different from the first format on the screen of the exterior terminal device.

17. A non-transitory storage medium storing a program executable by a computer to perform analysis function determination processing, the analysis function determination processing comprising:

analyzing input image data using a preset analysis function;

in a case in which a standby start-up request is received from an exterior terminal device, determining an analysis function to be a start-up target among a plurality of analysis functions based on an analysis result obtained by the preset analysis function and a preset condition, and starting up the determined analysis function in a background such that an analysis result of the determined analysis function is not able to be displayed and an icon corresponding to the determined analysis function is displayed in a first format on a screen of the exterior terminal device; and in a case in which a full start-up request is further received from the exterior terminal device in response to the icon corresponding to the determined analysis function being selected, fully starting up the determined start-up analysis function that has already been started up in the background such that the fully started-up analysis function and the analysis result thereof are able to be displayed and the icon corresponding to the determined analysis function is displayed in a second format different from the first format on the screen of the exterior terminal device.

\* \* \* \* \*